US00PP30292P2

(12) United States Plant Patent
Hansen

(10) Patent No.: US PP30,292 P2
(45) Date of Patent: Mar. 12, 2019

(54) ***COLOCASIA* PLANT NAMED 'DISTANT MEMORY'**

(50) Latin Name: ***Colocasia* hybrid**
Varietal Denomination: Distant Memory

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,164

(22) Filed: Feb. 14, 2018

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new cultivar of *Colocasia* plant named 'Distant Memory' characterized by large, lustrous, heavily-dimpled, dark greyed-purple leaves; stemless, vigorous, tropical, perennial habit forming multiple shoots at base and multiple long spadix flowers surrounded by enrolled burgundy spathes. The new plant is useful in the landscape as a specimen, en masse, or in a container in the home or in the landscape.

1 Drawing Sheet

Botanical classification: *Colocasia* hybrid.
Cultivar designation: 'Distant Memory'.

CROSS REFERENCE TO RELATED APPLICATIONS

This application is co-pending with the U.S. Plant Patent Applications for two other plants from the same breeding program with the same parents, namely, *Colocasia* plant named 'Black Goblet' U.S. Plant patent application Ser. No. 15/932,772 and *Colocasia* plant named 'Black Swan' U.S. Plant patent application Ser. No. 15/932,163.

BACKGROUND OF THE PLANT

The present invention relates to a new and distinct hybrid of *Colocasia*, hereinafter referred to by its cultivar name, 'Distant Memory'. *Colocasia* is a tropical genus in the Araceae family.

The new cultivar was derived from a controlled breeding program under the direction of the inventor at a wholesale perennial nursery in Zeeland, Mich., USA. The overall purpose of the breeding program was to make selections of *Colocasia* plants with colorful foliage, good growth rate that are well suited for landscape or containers. 'Distant Memory' arose from a cross performed in May 17, 2012 between *Colocasia* 'Black Coral' U.S. Plant Pat. No. 23,896 as the female and the male parent was 'Thailand Giant' (not patented). 'Distant Memory' was given the breeder code 12-07-02 prior to naming.

Asexual propagation of the new cultivar was first accomplished by division in 2013 and later by in vitro propagation using shoot tip culture in 2014. To those skilled in the art shoot tip tissue culture produces propagules of identical characteristics to those of the original plant. Asexual propagation of 'Black Swan' by shoot tip tissue culture has shown that the characteristics of the new cultivar are stable and reproduce true to type in successive generations.

No plants of *Colocasia* 'Distant Memory' have been sold, in this country or anywhere in the world, prior to the filing of this application, nor has any disclosure of the new plant been made prior to the filing of this application except that which was disclosed within one year of the filing of this application, and was either derived directly or indirectly from the inventor.

SUMMARY OF THE INVENTION

Plants of *Colocasia* 'Distant Memory' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of the new plant and distinguish it as a new and distinct *Colocasia* different from all other *Colocasia* known to the inventor:

1. Large, lustrous, heavily-dimpled, dark greyed-purple leaves;
2. Medium to large, upright, stemless, vigorous, tropical perennial habit;
3. Multiple shoots forming at base;
4. Multiple, long, spadix per leaf axil.

BRIEF DESCRIPTION OF THE DRAWINGS

The photograph of the new plant demonstrates the unique traits and the overall appearance of *Colocasia* 'Distant Memory'. The colors are as accurate as reasonably possible with color reproductions of this type. Variations in ambient light spectrum, source and direction may cause the appearance of minor variation in color. The plants used in the photograph were two-year-old plants grown initially in a greenhouse then set out in early summer in a shaded trial garden at a wholesale perennial nursery in Zeeland, Mich. with supplemental water and fertilizer when needed. No plant growth regulators or pinching have been used.

Figure 1:
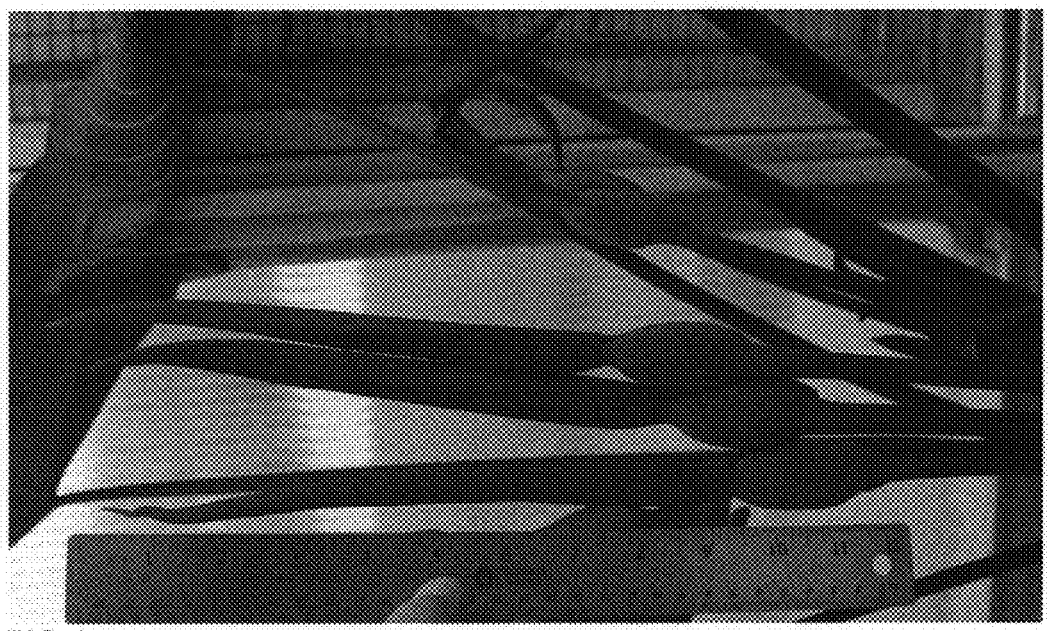
FIG. 1 shows a close-up of the flower with ruler for size reference.
Figure 2:
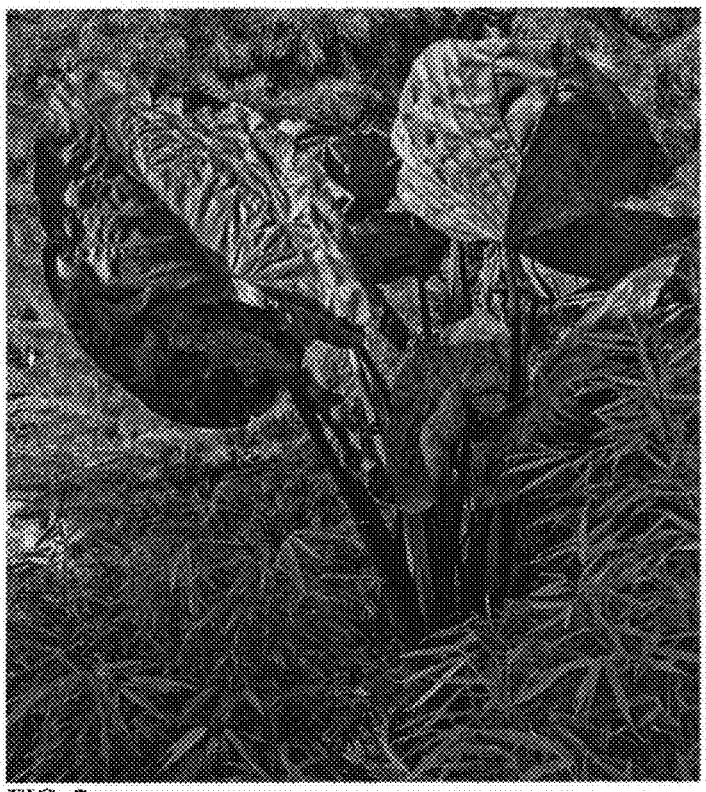
FIG. 2 shows the habit of the new plant with heavily dimpled leaf blades.

The nearest comparison varieties known to the inventor are the co-pending siblings and 'Black Sapphire Gecko' U.S. Plant Pat. No. 27,966.

In comparison to the female parent, 'Black Coral' the new plant is larger in habit and individual leaf blades, the leaf blades are more dimpled and held more horizontal in maturity and the plant habit produces greater number of side shoots filling out containers. In comparison to green-leafed male parent, 'Thailand Giant' the new plant is shorter with smaller leaves, has darker leaf blades and petioles and a lustrous adaxial leaf surface.

'Distant Memory' has larger leaf blades than 'Black Sapphire Gecko', the leaves are held more outright and less cernuous than 'Black Sapphire Gecko' and the new plant has more basal shoot development. Compared with 'Black Swan' the new plant is smaller in height and larger in width, with more basal side shoots filling in more at the base. Compared with 'Black Goblet' the new plant has a flatter and less cupped leaves, the leaves are more dimpled and the habit is broader with more basal side shoots.

DETAILED BOTANICAL DESCRIPTION

The following is a detailed description of two-year-old plants of the new cultivar as grown initially in a greenhouse and then outdoors for the summer of the second season, in a shaded trial garden in Zeeland, Mich. No plant growth regulators have been used. Plants of the new cultivar have not been tested under all possible conditions. The phenotype may vary with changes in environmental, climatic, and cultural conditions without change however in the genotype. The color reference is in accordance with the 2015 edition of The Royal Horticultural Society Colour Chart except where general color dictionary terms are used.

Botanical designation: *Colocasia* hybrid;

Cultivar denomination: 'Distant Memory';

Parentage: The female or seed parent is 'Black Coral' and the male or pollen parent is 'Thailand Giant';

Asexual propagation: Shoot tip tissue culture;

Time to initiate roots: About two weeks;

Time to finish in a 7 liter container: About three months from a 2.5 cm plug;

Growth rate: Vigorous;

Plant habit: Tropical herbaceous perennial; upright; acaulescent; upright; clumping; tuberous rhizomes formed at base of plant;

Plant size: About 140.0 cm tall and about 190 cm wide at edges of leaves;

Root description: Thick, fleshy, limited branching; to about 25.0 cm long;

Root color: Between RHS 182A and RHS 183D;

Foliage: Simple; alternate; petiolate; sagittate to cordate; slightly and irregularly undulate; dimpled; base cordate to auriculate, lobes frequently imbricate; apex broadly acute to slightly cuspidate; margin entire; adaxial surface lustrous; abaxial dull; both adaxial and abaxial glabrous;

Leaf size: Average about 62.0 cm long and about 40.0 cm across; base fused about 9.0 cm below petiole attachment; basal auricles extending about 16.0 cm below petiole;

Leaf attitude: Mostly outwardly to semi-upright;

Leaf color: While still partially convolute adaxial nearest RHS 146D with blushing of between RHS N186C and RHS N187B, abaxial nearest blend of RHS 146D and RHS 148D with slight blushing of between RHS N186C and RHS N186B; mature adaxial nearest RHS N186A, mature abaxial blend between RHS 189A and RHS N186C;

Veins: Pinnate; glabrous abaxial and adaxial; main veins broad, nearly smooth adaxial and costate and rounded abaxial; abaxial midrib to about 9.0 mm across, lateral pinnate veins to about 3.0 mm across and secondary veins less than 0.3 mm across; adaxial midrib about 8.0 mm across, lateral pinnate veins to about 2.5 mm across and secondary veins less defined dimension;

Vein color: Mature adaxial midrib and primary pinnate veins nearest RHS N187B and secondary adaxial same as surrounding leaf tissue; mature abaxial midrib and primary pinnate veins nearest RHS 187C proximally and nearest RHS 187A distally, secondary veins same as surrounding leaf tissue; emerging adaxial veins nearest RHS 195B, emerging abaxial veins nearest RHS 194D;

Petiole: Sarcous; concavo-convex to involute; petiole attitude upright to semi-outright; average of about 82.0 cm in length, about 35 mm deep near base, about 30.0 mm across laterally at base and 6 mm across at blade; glabrous, glaucous abaxial and adaxial becoming lustrous both surfaces;

Petiole color: Abaxial proximally blend between N186A and RHS 187A, distally becoming nearest RHS 187C; adaxial nearest blend between RHS 187A and RHS N186A laterally and toward center nearest RHS 187B;

Inflorescence description: Spadix with spathe; female portion proximal to male portion on same peduncle; beginning to bloom about mid-August once plants are mature; producing typically four inflorescences per leaf axil.

Inflorescence bud: Linear to clavate with swollen rounded base; apex narrowly acute; about 22.0 cm long and about 2.2 cm wide in swollen base;

Bud color: Variable; between RHS 187A and RHS 187B in distal areas and nearest RHS N187B in swollen base;

Inflorescence size: To about 29.0 cm in length and 2.7 cm wide in female portion and 1.9 cm wide in male portion;

Flower fragrance: None detected;

Lastingness of inflorescence: About 2 to 3 weeks.

Flower quantity: Average of about 200 female sessile flowers sessile to spadix; average about 500 sessile male flowers per spadix;

Spathe: Hooded convolute bract subtending spadix and completely enveloping spadix; lanceolate; with acute apex and truncate base; margin entire;

Spathe size: Average of about 22.0 cm in length, about 7.0 cm in width if unrolled and 15.0 mm diameter at base when rolled;

Spathe color: Abaxial nearest RHS N186D; adaxial nearest RHS 157B toward center and marginally becoming blushed with nearest RHS 186A to nearest RHS N186D on margin;

Spadix: Male portion with acute apex, average about 5.5 cm in length and 6.0 mm in width, color nearest RHS 157C; female portion ellipsoidal in shape, an average of 3.0 cm in length and 14.0 mm in width, color nearest RHS 161D;

Reproductive organs: Have not been observed to develop;

Fruit and seed: Have not been observed;

Diseases and resistance: Resistance to pests and diseases beyond that common for other *Colocasia* cultivars has not been observed. The new plant is tropical and grows best with ample moisture, good drainage and warm temperatures. The complete hardiness of the new plant has not been tested.

It is claimed:

1. A new and distinct cultivar of *Colocasia* plant named 'Distant Memory' as herein illustrated and described.

* * * * *